United States Patent
Ray et al.

(10) Patent No.: US 6,286,510 B1
(45) Date of Patent: Sep. 11, 2001

(54) APPARATUS AND METHOD FOR PREVENTING FLUID TRANSFER BETWEEN AN OVIDUCT AND A UTERINE CAVITY

(76) Inventors: Terry L. Ray, 1118 E. San Angelo Ave., Gilbert, AZ (US) 85234; James W. Zeluff, 11165 Sandy Grove Ave., Las Vegas, NV (US) 89144

(*) Notice: Subject to any disclaimer, the term of this patent is extended or adjusted under 35 U.S.C. 154(b) by 0 days.

(21) Appl. No.: 09/434,063

(22) Filed: Nov. 5, 1999

(51) Int. Cl.[7] ............................................. A61F 6/06
(52) U.S. Cl. ............................................. 128/830; 128/831
(58) Field of Search ................................. 128/830–841

(56) References Cited

U.S. PATENT DOCUMENTS

| | | |
|---|---|---|
| 404,019 | 5/1889 | Sperry . |
| 2,785,675 | 3/1957 | Berkman . |
| 3,675,639 | 7/1972 | Cimber . |
| 3,680,542 | 8/1972 | Cimber . |
| 3,858,571 | * 1/1975 | Rudolph .............................. 128/831 |
| 3,918,431 | 11/1975 | Sinnreich . |
| 4,365,621 | 12/1982 | Brundin . |
| 4,537,186 | 8/1985 | Verschoof . |
| 4,834,091 | 5/1989 | Ott . |
| 5,702,421 | 12/1997 | Schneidt . |
| 5,935,137 | * 8/1999 | Saadat .................................. 128/831 |
| 5,954,715 | * 9/1999 | Harrington ........................... 128/831 |

FOREIGN PATENT DOCUMENTS

| | | |
|---|---|---|
| 105669 | 4/1984 | (EP) . |
| 201072 8 | 7/1979 | (GB) . |
| 2010728 | * 7/1979 | (GB) . |

* cited by examiner

*Primary Examiner*—Michael A. Brown
(74) *Attorney, Agent, or Firm*—Parsons & Goltry; Robert A. Parsons; Michael W. Goltry

(57) ABSTRACT

Apparatus for preventing fluid transfer through an opening connecting an oviduct to a uterine cavity comprising an insert for insertion into the oviduct through the opening leading from the uterine cavity to the oviduct, a seal carried by the insert for engaging uterine tissue leading to the opening and receiving fibroblast ingrowth to create a hermetic seal between the oviduct and the uterine cavity, and an engagement element supported by the insert for securing the insert to the oviduct.

26 Claims, 2 Drawing Sheets

APPARATUS AND METHOD FOR PREVENTING FLUID TRANSFER BETWEEN AN OVIDUCT AND A UTERINE CAVITY

FIELD OF THE INVENTION

This invention concerns birth control apparatus and methods and, more particularly, apparatus and methods for preventing fluid transfer between a uterine cavity and an oviduct of a female reproductive system.

BACKGROUND OF THE INVENTION

Most acceptable forms of birth control comprise apparatus and methods for preventing conception. While certain prescription drugs can adequately prevent conception from occurring, skilled artisans have devoted considerable attention toward less expensive mechanical devices and techniques. Nearly all mechanical birth control devices and techniques attempt to block fluid transfer between the vagina and the uterus, or the oviducts and the uterus. By preventing fluid transfer between the vagina and the uterus and/or the oviducts and the uterus, conception is prevented or at least minimized. Although existing mechanical devices and techniques prove adequate, they can be difficult to construct, challenging to install and unreliable. Given these and other deficiencies in the art, the need for certain new and useful improvements is evident.

Accordingly, it would be highly desirable to provide improved apparatus and methods for preventing fluid transfer between an oviduct and a uterine cavity of a female productive system.

It is a purpose of the invention to provide new and improved apparatus that are easy to construct.

It is another purpose of the invention to provide new and improved apparatus that are easy to use.

It is still another purpose of the invention to provide new and improved apparatus that are inexpensive.

It is a further provision of the invention to provide new and improved apparatus that may be installed in minimally invasive surgical technique.

It is still a further provision of the invention to prevent unwanted pregnancies.

It is yet still a further purpose of the invention to provide new and improved apparatus that are easy to install.

It is yet a further purpose of the invention to provide new and improved apparatus that are not damaging to the female reproductive system.

It is another purpose of the invention to provide new and improved apparatus that are highly reliable for preventing fluid transfer between an oviduct and a uterine cavity of a female reproductive system.

SUMMARY OF THE INVENTION

The above problems and others are at least partially solved and the above purposes and others realized in new and improved apparatus for preventing fluid transfer through an opening connecting an oviduct to a uterine cavity. The apparatus is comprised of an insert for insertion into the oviduct through the opening leading from the uterine cavity to the oviduct, a seal carried by the insert for engaging uterine tissue leading to the opening and receiving fibroblast ingrowth to create a hermetic seal between the oviduct and the uterine cavity, and an engagement element supported by the insert for securing the insert to the oviduct. The engagement element may comprise an enlargement or a toothed, furrowed or rigged surface. The engagement element allows for the insertion of the insert into the opening and the oviduct, and inhibits the insert from falling away from the oviduct through the opening after installation. The insert supports a ball joint that may be grasp by a tool and which allows the apparatus to deflect during installation. The ball joint is carried by a cap supported by an extension of the insert. The cap defines a continuous bead that extends into and displaces the seal forming a sealing engagement between the cap and the extension.

Consistent with the foregoing, associated methods of preventing fluid transfer through an opening connecting an oviduct to a uterine cavity may also be provided.

BRIEF DESCRIPTION OF THE DRAWINGS

The foregoing and further and more specific objects and advantages of the invention will become readily apparent to those skilled in the art from the following detailed description thereof taken in conjunction with the drawings in which.

DETAILED DESCRIPTION OF A PREFERRED EMBODIMENT

Figure 1:
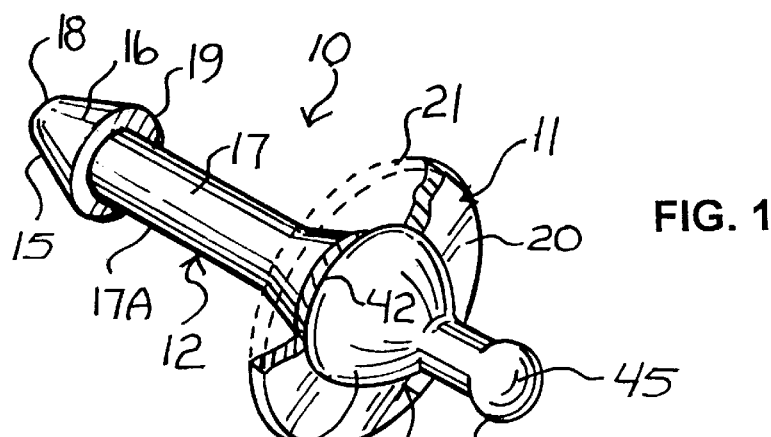
FIG. 1 is a perspective view of apparatus for preventing fluid transfer between an oviduct and a uterine cavity of a female reproductive system.
Figure 2:
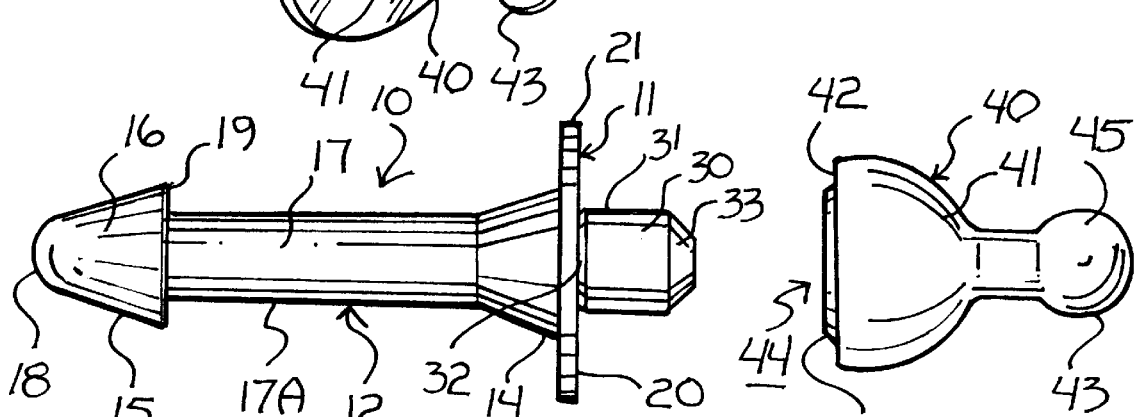
FIG. 2 is an exploded side view of the apparatus of FIG. 1.

Turning now to the drawings, in which like reference characters indicate corresponding elements throughout the several views, attention is first directed to FIG. 1 illustrating a perspective view of apparatus 10 for preventing fluid transfer between an oviduct and a uterine cavity of a female reproductive system. Apparatus 10 is comprised of a stop or seal 11 supported by an insert 12. Referring also to FIG. 2, insert 11 is constructed of rigid, non-porous, bio-compatible material such as stainless steel, titanium, ceramics or a polybase material. Insert 11 is comprised of a shaft 17 that is elongate. Shaft 17 has a proximal extremity 14, a free or distal extremity 15, and supports an enlargement 16. In this embodiment, enlargement 16 is conical and is positioned at or adjacent distal extremity 15. Enlargement 16 leads with a point or vertex 18 that is somewhat rounded, and trails with a base or directrix 19 that defines a step angle with shaft 17. Directrix 19 faces proximal extremity 14 and defines a diameter greater than outer diameter 17A of shaft 17.

Seal 11 is comprised of a continuous annular body 20. In this embodiment, body 20 encircles insert 12 at or adjacent proximal extremity 14 and includes an outer diameter or continuous extremity 21 greater than that of directrix 19 and shaft 17. Body 20 is preferably fabricated of a somewhat or highly deformable, porous material. In a preferred embodiment, body 20 is constructed of polytetrafluoroethylene (PTFE) plastic which is a well-known existing material sold under the trademark TEFLON. Appropriate porous PTFE materials are commercially available and may be produced by the process described in Japanese Patent Publication No. 135,60/67 and U.S. Pat. No. 3,953,566, which are incorporated by reference herein. Other acceptable porous materials manufactured and sold under the trademarks PROPLAST or GORTEX may also be used for body 20. Included in a list of preferred materials for body 20 is cotton, polypropylene or silk mesh. Body 20 defines micro porous fibrous structure consisting of small fibers and nodes connected together. Similar expanded PTFE products are presently in use for vascular prostheses and typically include pore sizes on the order of two microns or greater. Typical pore size for most effective utilization in vascular prostheses generally fall within the range of between approximately five to ten microns.

Regarding FIG. 2, insert 12 further includes an extension 30 that extends away from proximal extremity 14. In a preferred embodiment, extension 30 defines an outer diameter or continuous extremity 31 substantially equal to outer diameter 17A of shaft 17, a continuous beveled edge 32 facing proximal extremity 14 and a continuous beveled edge 33 spaced and facing away from proximal extremity 14. The outer diameter of extension 30 may, of course, be of any desired size. A cap 40 is also provided. Cap 40 is comprised of a body 41 having an inner end 42, an outer end 43, a socket 44 extending into inner end 42 and a ball joint 45 positioned, in this specific embodiment, at or adjacent outer end 42. A continuous extension or bead 46 extends away from inner end 42 bounding the opening leading to socket 44. Cap 40 is designed to fit over extension 30 in a supported condition. Socket 44 is, therefore, sized to accommodate extension 30. Beveled edge 33 allows extension 30 to guide easily into socket 44, and the fit between extension 30 and socket 44 preferably close or tight, like a press fit. When properly installed, bead 46 extends into body 20 displacing it against beveled edge 32 to form a seal between cap 40 and extension 30 and, more particularly, between bead 46 and beveled edge 32.

Figure 3:
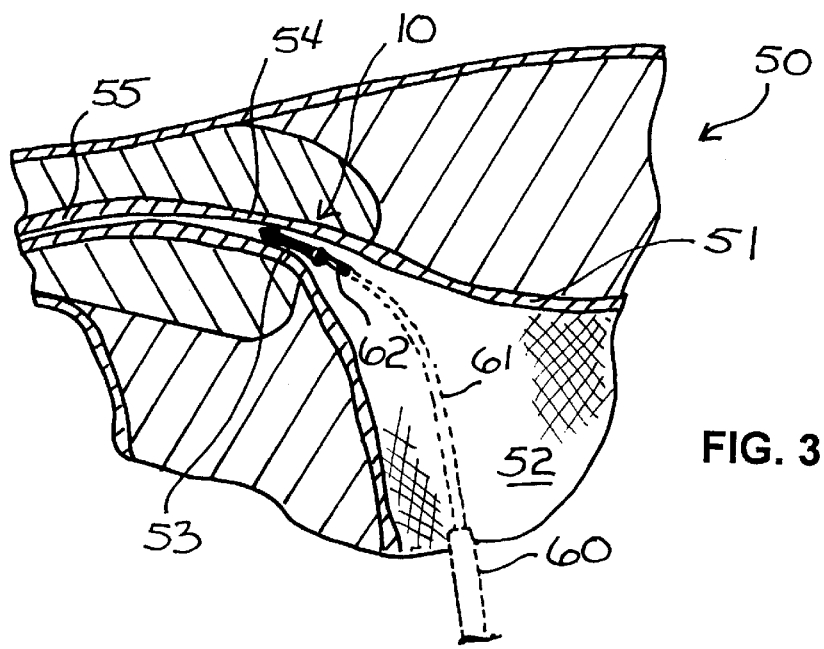
FIG. 3 is a view showing the apparatus of FIG. 1 as it would appear being installed.

Regarding FIG. 3, shown is fragmented sectional view of a female reproductive system 50 including a uterus 51 bounding a uterine cavity 52, and an opening 53 leading to an isthmus 54 of an oviduct 55. To install apparatus 10, a guide catheter 60 may be maneuvered into uterine cavity 52 by way of the vagina and the cervix. Catheter 60 is preferably flexible which allows it to be easily maneuvered into the uterine cavity 52. Catheter 60 preferably comprises the operating channel of a hysteroscope, which is a commercially available device used primarily by gynecologists for examining and operating on the female reproductive system. A typical hysteroscope typically includes three parallel oriented channels that run longitudinally along a given length of the device. One of these channels provides a source of illumination, and second channel includes a fiberoptic bundle that provides illumination. The third channel can house a flexible guide 61 having flexible jaws or tongs 62 that can engage ball joint 45. Guide 61 includes a mechanism that a physician may operate for moving tongs 62 between an open condition and a closed condition for engaging ball joint 45. By maneuvering guide 61 through catheter 60, apparatus 10 may be inserted, distal extremity 15 first, into and through opening 53. Ball joint 45 permits apparatus 10 to move, deflect or articulate as needed relative to tongs 62 for providing a natural and easy alignment and insertion of insert 12 into oviduct 55 through opening 53. The fiberoptic bundle and the illuminating ability of catheter 60 allows the physician to visually identify opening 53.

Figure 4:
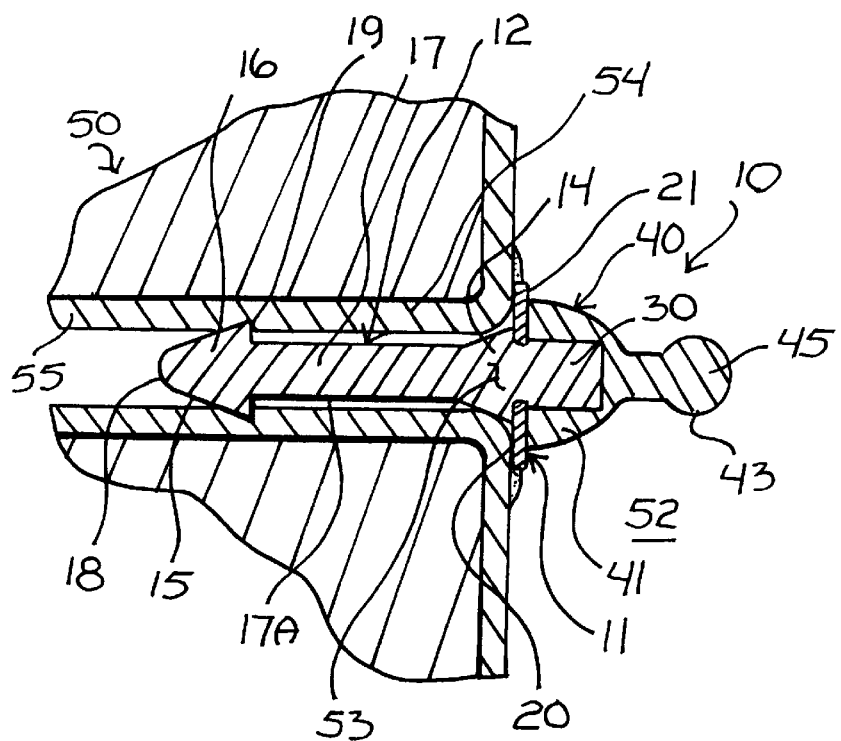
FIG. 4 is a view showing the apparatus as it would appear installed with a female reproductive system for preventing fluid transfer between an oviduct and a uterine cavity.

With vertex 18 facing opening 53, insert may be easily inserted into oviduct 55 through opening 53. The blunt or rounded vertex 18 provides for a smooth insertion into oviduct 55 through opening 53. Although directrix 19 is enlarged, it will readily pass into oviduct 55 through opening 53 as it trails vertex. However, seal 11 is of a size too great to pass through opening 53, and rests against the surface of uterine tissue leading to and defining opening 53 as shown in FIG. 4. Insert 12 maintains a desired alignment between seal and the uterine tissue leading to and defining opening 53. Once insert 12 is inserted into oviduct 55 with seal 11 positioned against the uterine tissue leading to and defining opening 53, fibroblast ingrowth between that surrounding uterine tissue and seal 11 commences immediately to form an initially weak but progressively stronger bond between seal 11 and the uterine tissue. Directrix 19 is directed against and engages or impinges into the inner surface of oviduct 55. Because directrix 19 is directed toward opening 53, insert 12 cannot be easily moved out of oviduct 55 for directrix 19 digging or impinging into oviduct 55 tissue, which prevents insert 12 from inadvertently falling away from oviduct 55. Accordingly, enlargement 16, and especially directrix 19, functions as an engagement element that holds insert 12 in place so that seal 11 can accept immediate fibroblast ingrowth to provide a hermetic seal and fluid isolation between oviduct 55 and uterine cavity 52. The seal between bead 46 and beveled edge 32 further ensures fluid isolation between oviduct 55 and uterine cavity 52. Although enlargement 16 is positioned at or adjacent distal extremity 15, it may be positioned at other locations along insert 12 between the proximal and distal extremities 14 and 15. To remove apparatus 10, even after fibroblast ingrowth is complete, ball joint 45 may be grasped, such as with tongs 62, and apparatus 10 forcibly removed. Because uterine and oviduct tissue is very resilient, tissue damage caused by the forcible removable of apparatus 10 heals very quickly. Enlargement 16 may be provided in any desired size suitable for providing the described impingement against the inner surface of an oviduct.

Figure 5:
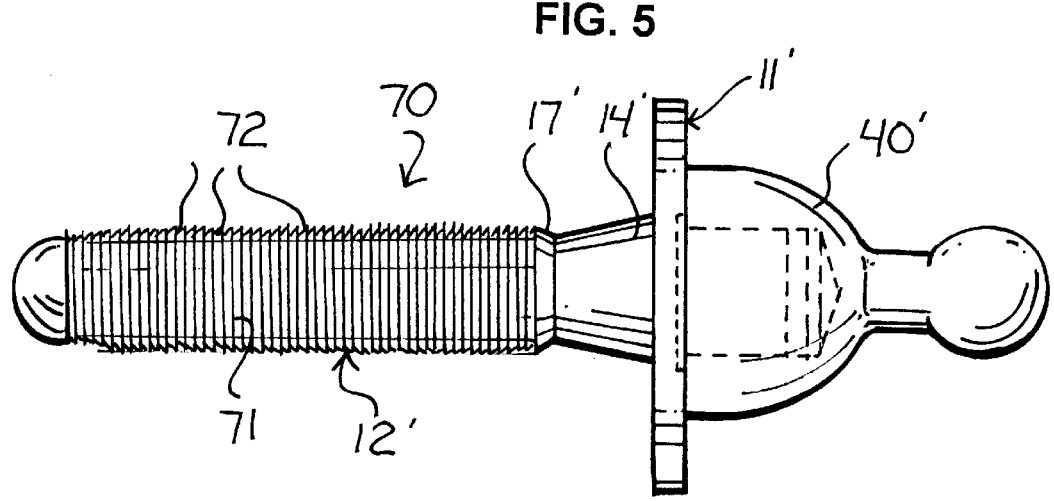
FIG. 5 is a side view of another embodiment of an apparatus for preventing fluid transfer between an oviduct and a uterine cavity of a female reproductive system.

FIG. 5 illustrates an alternate embodiment of apparatus 70 for preventing fluid transfer between an oviduct and a uterine cavity of a female reproductive system. Apparatus 70 is substantially identical to apparatus 10 in structure and function, and includes substantially the same elements. Accordingly, the reference characters used to describe apparatus 10 will also be used to describe apparatus 70, but only to the extent of their common structural components. For clarity, common reference characters used to describe apparatus 70 will include a prime ("'") symbol. In this regard, apparatus 70 includes seal 11, insert 12', proximal extremity 14', distal extremity 15', shaft 17' and cap 40' as previously described. Rather than providing insert 12' with an engagement element defined as an enlargement, shaft 17' defines a textured outer surface 71 between the proximal and distal extremities 14' and 15'. In this embodiment, textured outer surface 71 is continuous and is defined by a plurality of teeth 72. Teeth 72 are aligned in series between the proximal and distal extremities 14' and 15'. Each one of teeth 72 is continuous and is directed or slanted toward proximal extremity 14'. Because teeth 72 are each directed toward proximal extremity 14', insert 12 may easily be inserted into an oviduct in a direction leading with distal extremity 15'. Distal extremity 15' is defined as somewhat rounded or blunt, which facilitates easy insertion into an oviduct. When positioned in an oviduct, teeth 72 impinge against the inner surface of the oviduct and direct toward the opening leading to the oviduct. As a result, insert 12' cannot be easily moved out of the oviduct for the teeth 72 digging or impinging into the oviduct 55 tissue, which prevents insert 12' from inadvertently falling away from the oviduct. Like enlargement 16, teeth 72 cooperate together as an engagement element that holds insert 12' in place so that seal 11' can accept immediate fibroblast ingrowth to provide a hermetic seal and fluid isolation between the oviduct and the uterine cavity.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Apparatus for preventing fluid transfer through an opening connecting an oviduct to a uterine cavity, the apparatus comprising:
   an insert for insertion into the oviduct through the opening leading from the uterine cavity to the oviduct;
   a seal formed of a porous material and carried by the insert for engaging tissue proximate the opening and receiving fibroblast ingrowth to create a hermetic seal between the oviduct and the uterine cavity; and
   an engagement element supported by the insert for securing the insert to the oviduct.

2. Apparatus of claim 1, wherein the engagement element comprises an enlargement.

3. Apparatus of claim 2, wherein the enlargement is positioned adjacent a free extremity of the insert.

4. Apparatus of claim 3, wherein the enlargement is conical.

5. Apparatus of claim 1, wherein the engagement element comprises a textured surface.

6. Apparatus of claim 5, wherein the textured surface is continuous.

7. Apparatus of claim 5, wherein the textured surface comprises a tooth ed surface.

8. Apparatus of claim 1, wherein the engagement element allows for the insertion of the insert into the opening and the oviduct, and inhibits the insert from falling away from the oviduct through the opening.

9. Apparatus of claim 1, further including a ball joint, supported by the insert, that may be grasp by a tool and which allows the apparatus to deflect during installation.

10. Apparatus of claim 9, wherein the ball joint is carried by a cap supported by an extension of the insert.

11. Apparatus of claim 10, wherein the cap defines a continuous bead that extends into and displaces the seal forming a sealing engagement between the cap and the extension.

12. Apparatus of claim 1, wherein the seal is formed of a biocompatible material that stimulates ingrowth of fibroblastic tissue.

13. Apparatus of claim 1, wherein the insert is fabricated of a rigid, non-porous bio-compatible material.

14. Apparatus for preventing fluid transfer through an opening connecting an oviduct to a uterine cavity, the apparatus comprising:
   an insert for insertion into the oviduct through the opening leading from the uterine cavity to the oviduct;
   a seal formed of a porous material and carried by the insert for engaging uterine tissue leading to the opening and receiving fibroblast ingrowth to create a continuous hermetic seal; and
   an engagement element supported by the insert for engaging the oviduct and maintaining the seal in engagement to the uterine tissue leading to the opening.

15. Apparatus of claim 14, wherein the engagement element comprises an enlargement.

16. Apparatus of claim 15, wherein the enlargement is positioned adjacent a free extremity of the insert.

17. Apparatus of claim 16, wherein the enlargement is conical.

18. Apparatus of claim 14, wherein the engagement element comprises a textured surface.

19. Apparatus of claim 18, wherein the textured surface is continuous.

20. Apparatus of claim 18, wherein the textured surface comprises a toothed surface.

21. Apparatus of claim 14, wherein the engagement element allows for the insertion of the insert into the opening and the oviduct, and inhibits the insert from falling away from the oviduct through the opening.

22. Apparatus of claim 14, wherein the insert supports a ball joint that may be grasp by a tool and which allows the apparatus to deflect during installation.

23. Apparatus of claim 22, wherein the ball joint is carried by a cap supported by an extension of the insert.

24. Apparatus of claim 23, wherein the cap defines a continuous bead that extends into and displaces the stop forming a sealing engagement between the cap and the extension.

25. Apparatus of claim 14, wherein the stop is formed of a biocompatible material that stimulates ingrowth of fibroblastic tissue.

26. Apparatus of claim 14, wherein the insert is fabricated of a rigid, non-porous, bio-compatible material.

* * * * *